US007655412B2

(12) United States Patent
Mackenzie et al.

(10) Patent No.: US 7,655,412 B2
(45) Date of Patent: Feb. 2, 2010

(54) SELF-ASSEMBLY MOLECULES

(75) Inventors: C. Roger Mackenzie, Ottawa (CA); Jianbing Zhang, Ottawa (CA)

(73) Assignee: National Research Council of Canada, Ottawa (CA)

( * ) Notice: Subject to any disclaimer, the term of this patent is extended or adjusted under 35 U.S.C. 154(b) by 6 days.

(21) Appl. No.: 10/496,845

(22) PCT Filed: Nov. 29, 2002

(86) PCT No.: PCT/CA02/01829

§ 371 (c)(1), (2), (4) Date: May 27, 2004

(87) PCT Pub. No.: WO03/046560

PCT Pub. Date: Jun. 5, 2003

(65) Prior Publication Data

US 2006/0051292 A1 Mar. 9, 2006

(51) Int. Cl.
*G01N 33/53* (2006.01)
(52) U.S. Cl. .......................... 435/7.1; 435/7.2; 436/517
(58) Field of Classification Search .................. 435/7.1, 435/7.2, 7.92; 436/518, 574, 86
See application file for complete search history.

(56) References Cited

U.S. PATENT DOCUMENTS

| | | | | |
|---|---|---|---|---|
| 4,208,479 | A * | 6/1980 | Zuk et al. | 435/7.9 |
| 5,744,346 | A * | 4/1998 | Chrysler et al. | 435/226 |
| 5,837,242 | A * | 11/1998 | Holliger et al. | 424/136.1 |
| 5,919,643 | A * | 7/1999 | Kelley et al. | 435/19 |
| 5,955,293 | A * | 9/1999 | Keusch et al. | 435/7.92 |
| 6,310,043 | B1 * | 10/2001 | Bundle et al. | 514/25 |
| 6,485,726 | B1 * | 11/2002 | Blumberg et al. | 424/178.1 |
| 6,548,066 | B1 * | 4/2003 | Michaeli et al. | 424/185.1 |
| 7,385,032 | B2 | 6/2008 | Tschopp et al. | |
| 2002/0041865 | A1 * | 4/2002 | Austin et al. | 424/85.2 |

FOREIGN PATENT DOCUMENTS

| | | |
|---|---|---|
| WO | WO 0061183 | * 10/2000 |
| WO | WO-0127144 | 4/2001 |
| WO | WO-0149866 | 7/2001 |

OTHER PUBLICATIONS

Davies et al. (Protein Engineering 1996, vol. 9, p. 531-537).*
Plückthun, A., et al., "New protein engineering approaches to multivalent and bispecific antibody fragments", *Immunotechnology* *3* (1997) 83-105.

(Continued)

*Primary Examiner*—Jacob Cheu
(74) *Attorney, Agent, or Firm*—Blank Rome LLP

(57) ABSTRACT

There is provided a method of forming a multimeric complex having affinity for a target. The method comprises: obtaining a plurality of self-assembly molecules, said self-assembly molecules including complementary self-assembly units such as verotoxin subunit B, each of which is operatively connected to an interaction domain such as a single domain antibody specific for the target; and combining said self-assembly molecules such that at least three said self-assembly units simultaneously bind to one another so as to permit the single domain antibodies to bind the target.

11 Claims, 11 Drawing Sheets

OTHER PUBLICATIONS

Figure 1:
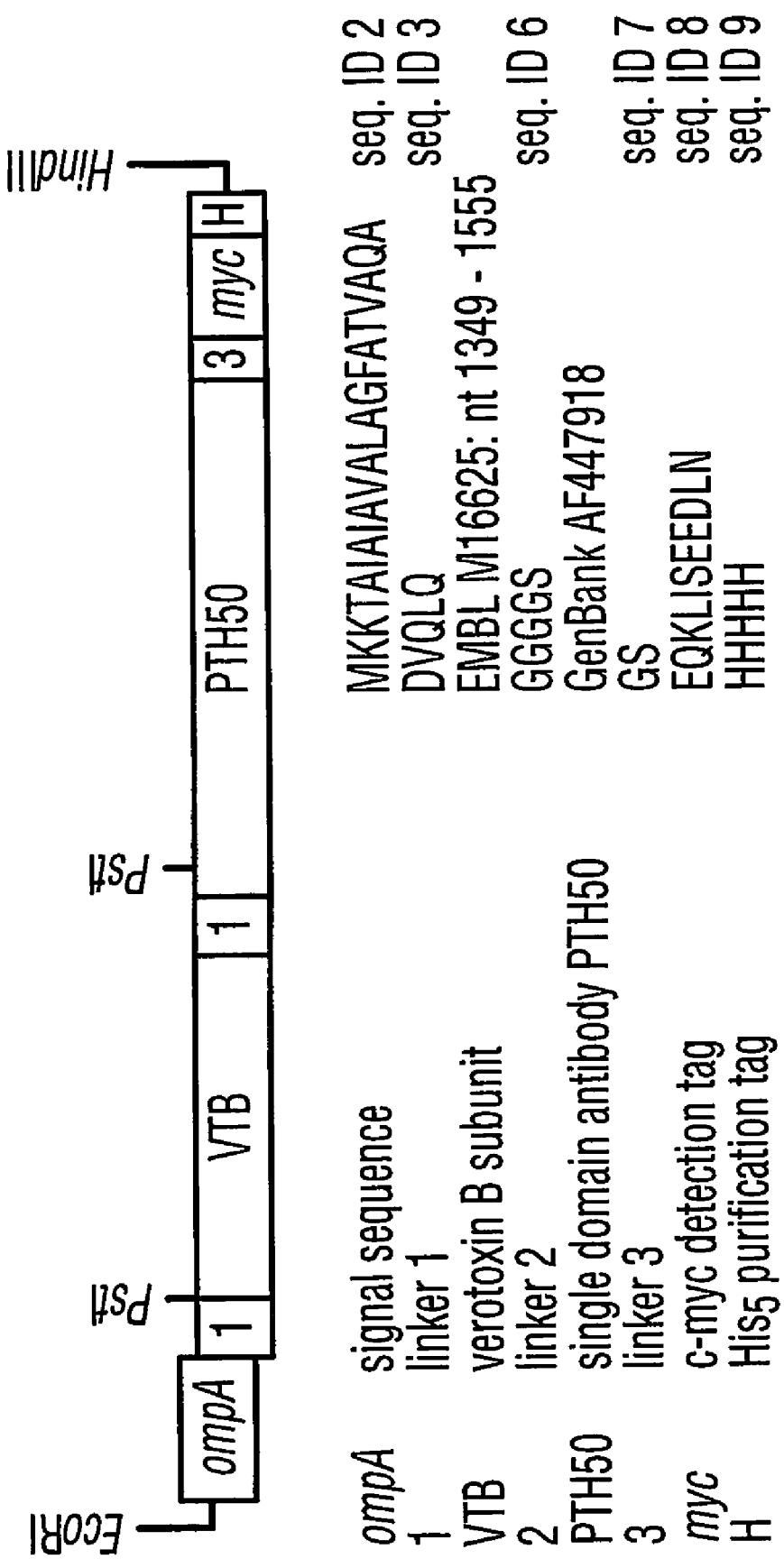

Terskikh, A.V., et al., ""Peptabody": A new type of high avidity binding protein", *Proc. Natl. Acad. Sci. USA, Biochemistry*, Mar. 1997, vol. 94, pp. 1663-1668.

Efimov, V.P., et al., "The thrombospondin-like chains of cartilage oligomeric matrix protein are assembled by a five-stranded α-helical bundle between residues 20 and 83", *FEBS Letters 341* (1994) 54-58.

Hudson, P.J., et al., "High avidity scFv multimers; diabodies and triabodies", *Journal of Immunological Methods 231* (1999) 177-189.

Kaminski, M.J., et al., "The Role of Homophilic Binding in Anti-tumor Antibody R24 Recognition of Molecular Surfaces", *The Journal of Biological Chemistry*, vol. 274, No. 9, Issue of Feb. 26, 1999, pp. 5597-5604.

Soltyk, A,M., et al., A Mutational Analysis of the Glogotriaosylceramide-binding Sites of Verotoxin VT1, *The Journal of Biological Chemistry*, vol. 277, No. 7, Issue of Feb. 15, 2002, pp. 5351-5359.

Yang, W., et al., "CDR Walking Mutagenesis for the Affinity Maturation of a Potent Human Anti-HIV-1 Antibody into the Picomolar Range", *J. Mol. Biol.* (1995) 254, 392-403.

Schier, R., et al., "Isolation o Picomolar Affinity Anti-c-erbB-2 Single-chain Fv by Molecular Evolution of the Complementarity Determining Regions in the Center of the Antibody Binding Site", *J. Mol. Biol.* (1996) 263, 551-567.

Ohlin, M., et al., "Light Chain Shuffling of a High Affinity Antibody results in a Drift in Epitope Recognition", *Molecular Immunology*, 1996, vol. 33, No. 1., pp. 47-56.

McCafferty, J., et al., "Phage antibodies: filamentous phage displaying antibody variable domains", *Nature*, vol. 348, Dec. 6, 1990, pp. 552-554.

Griffiths, A.D., et al., "Isolation of high affinity human antibodies directly from large synthetic repertoires", *The EMBO Journal*, 1994, vol. 13, No. 14, pp. 3245-3260.

Hoogenboom, H.R., et al., "Natural and designer binding sites made by phage display technology", *Immunology Today*, Aug. 2000, vol. 21, No. 8, 371-378.

Tanha, J., et al., "Selection by phage display of llama conventional $V_H$ fragments with heavy chain antibody $V_H$H properties", *Journal of Immunological Methods 263* (2002) 97-109.

Ling, H., et al., "Structure of the Shiga-like Toxin I B-Pentamer Complexed with an Analogue of Its Receptor $Gb_3$", *Biochemistry* 1998, 37, 1777-1788.

Sambrook, J., et al., *Molecular Cloning—A Laboratory Manual*, vol. 3, Third Edition.

Skerra A., et al., "The Functional Expression of Antibody $F_v$ Fragments in *Escherichia coli*: Improved Vectors and a Generally Applicable Purification Technique", *Biotechnology*, vol. 9, Mar. 1991, 273-278.

Willuda, J., et al., "High Thermal Stability is Essential for Tumor Targeting of Antibody Fragments: Engineering of a Humanized Anti-epithelial Glycoprotein-2 (Epithelial Cell Adhesion Molecule) Single-Chain Fv Fragment", *Cancer Research 59*, 5758-5767, Nov. 15, 1999.

Tanha, J., et al., "Optimal Design Features of Camelized Human Single-domain Antibody Libraries", *The Journal of Biological Chemistry*, vol. 276, No. 27, Issue of Jul. 6, 2001, pp. 24774-24780.

Kitov, P.I., et al., "Shiga-Like toxins are neutralized by tailored multivalent carbohydrate ligands", *Nature*, vol. 403, Feb. 10, 2000, 669-672.

Facchini et al., Experimental Cell Research 269:117-129 (2001).

* cited by examiner

FIG. 2C(i)
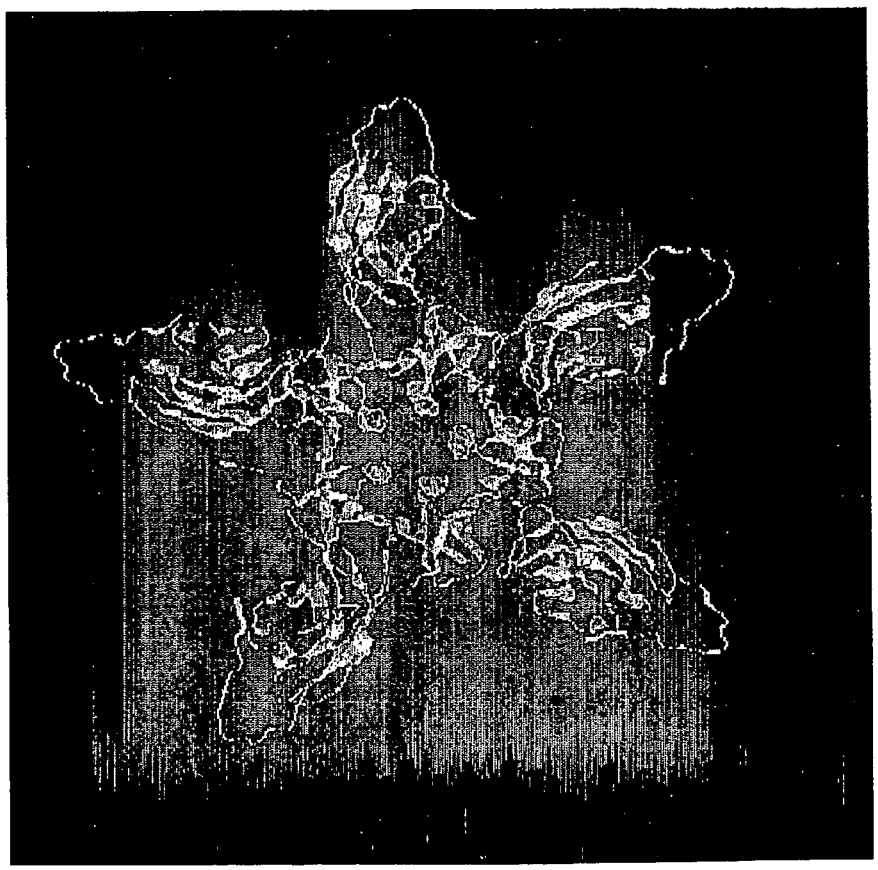
FIG. 2C(ii)

SEQ.ID. NO. 1:

¹SVSEIQLMHNLGKHLNSMERVEWLRKLLQDV³¹

SEQ. ID. NO. 2:

MKKTAIAIAVALAGFATVAQA

SEQ. ID. NO. 3:

DVQLQ

SEQ ID NO.4:

DVQLQASGGGSVQAGDSLRLSCAASGRPFSSFAMGWFRQAPGKEREFVAAISA
SGGETYYTGSLKGRFTISRDNAKNTVYLQMDSLKPEDTGVYYCAATINGAARRG
QGTQVTVSS

SEQ ID NO. 5:

GATGTGCAGCTGCAGGCGTCTGGGGGAGGATCGGTGCAGGCTGGGGACTCT
CTGAGACTCTCCTGTGCAGCCTCTGGACGCCCCTTCAGTAGCTTTGCCATGG
GCTGGTTCCGCCAGGCTCCAGGAAAGGAGCGTGAGTTTGTAGCTGCTATTAG
CGCGAGTGGTGGCGAGACATACTATACCGGCTCCCTGAAGGGCCGATTCAC
CATCTCCAGAGACAACGCCAAGAACACGGTATATCTGCAAATGGACAGCCTG
AAACCTGAGGATACAGGCGTCTATTACTGTGCAGCCACCATTAACGGGGCGG
CCCGACGAGGCCAGGGGACCCAGGTCACCGTCTCCTCA

SEQ. ID. NO. 6:

GGGGS

SEQ. ID. NO. 7:

GS

SEQ. ID. NO. 8:

EQKLISEEDLN

SEQ. ID. NO. 9:

HHHHH

FIG. 6

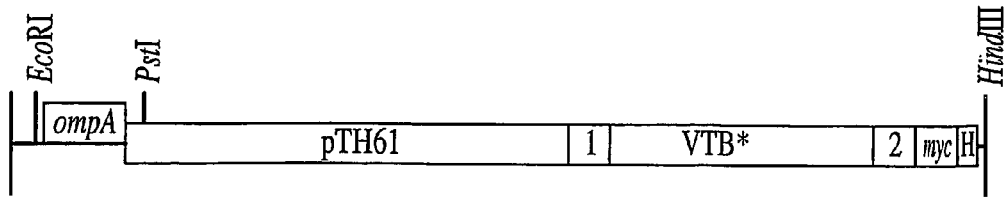
| | | |
|---|---|---|
| *ompA*: | ompA leading sequence | MKKTAIAIAVALAGFATVAQA |
| PTH61 | single domain antibody PTH61 | TREMBL:AF447920 |
| 1 | spacer 1 | GPGGGSGGGGS |
| VTB* | D17E/W34A mutant of VTB | VTB: Swissnew:P08027, AA21-89 |
| 2 | spacer 2 | GGGGSGLAGS |
| *myc* | antigenic region of C-myc | EQKLJSEEDLN |
| H | His-Tag | HHHHHH |
FIG. 9
FIG. 10

```
                       SEQUENCE LISTING

<160> NUMBER OF SEQ ID NOS: 11

<210> SEQ ID NO 1
<211> LENGTH: 31
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln Asp Val
            20                  25                  30

<210> SEQ ID NO 2
<211> LENGTH: 21
<212> TYPE: PRT
<213> ORGANISM: Escherichia coli

<400> SEQUENCE: 2

Met Lys Lys Thr Ala Ile Ala Ile Ala Val Ala Leu Ala Gly Phe Ala
1               5                   10                  15

Thr Val Ala Gln Ala
            20

<210> SEQ ID NO 3
<211> LENGTH: 5
<212> TYPE: PRT
<213> ORGANISM: llama

<400> SEQUENCE: 3

Asp Val Gln Leu Gln
1               5

<210> SEQ ID NO 4
```

<211> LENGTH: 116
<212> TYPE: PRT
<213> ORGANISM: llama

<400> SEQUENCE: 4

Asp Val Gln Leu Glu Ala Ser Gly Gly Ser Val Gln Ala Gly Asp
1               5                   10                  15

Ser Leu Arg Leu Ser Cys Ala Ala Ser Gly Arg Pro Phe Ser Phe
                20                  25                  30

Ala Met Gly Trp Phe Arg Gln Ala Pro Gly Lys Glu Arg Glu Phe Val
            35                  40                  45

Ala Ala Ile Ser Ala Ser Gly Gly Glu Thr Tyr Tyr Thr Gly Ser Leu
        50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Gly Val Tyr Tyr Cys
                85                  90                  95

Ala Ala Thr Ile Asn Gly Ala Ala Arg Arg Gly Gln Gly Thr Glu Val
            100                 105                 110

Thr Val Ser Ser
        115

<210> SEQ ID NO 5
<211> LENGTH: 348
<212> TYPE: DNA
<213> ORGANISM: llama

<400> SEQUENCE: 5
gatgtgcagc tgcaggcgtc tgggggagga tcggtgcagg ctggggactc tctgagactc      60
tcctgtgcag cctctggacg ccccttcagt agctttgcca tgggctggtt ccgccaggct     120
ccaggaaagg agcgtgagtt tgtagctgct attagcgcga gtggtggcga gacatactat     180
accggctccc tgaagggccg attcaccatc tccagagaca cgccaagaa cacggtatat     240 ctgcaaatgg acagcctgaa acctgaggat acaggcgtct attactgtgc agccaccatt     300
aacggggcgg cccgacgagg ccaggggacc caggtcaccg tctcctca                 348

<210> SEQ ID NO 6
<211> LENGTH: 5
<212> TYPE: PRT
<213> ORGANISM: Artificial sequence
<220> FEATURE:
<223> OTHER INFORMATION: artificial sequence

<400> SEQUENCE: 6

Gly Gly Gly Gly Ser
1               5

<210> SEQ ID NO 7
<211> LENGTH: 2
<212> TYPE: PRT
<213> ORGANISM: Artificial sequence
<220> FEATURE:
<223> OTHER INFORMATION: artificial sequence

<400> SEQUENCE: 7

Gly Ser
1

<210> SEQ ID NO 8
<211> LENGTH: 11

-continued

```
<212> TYPE: PRT
<213> ORGANISM: Homo sapiens

<400> SEQUENCE: 8

Glu Gln Lys Leu Ile Ser Glu Glu Asp Leu Asn
1               5                   10

<210> SEQ ID NO 9
<211> LENGTH: 13
<212> TYPE: PRT
<213> ORGANISM: llama

<400> SEQUENCE: 9

Leu Ile Ser Glu Glu Asp Leu Asn His His His His His
1               5                   10

<210> SEQ ID NO 10
<211> LENGTH: 7
<212> TYPE: PRT
<213> ORGANISM: Escherichia coli

<400> SEQUENCE: 10

Gly Pro Gly Gly Gly Gly Ser
1               5

<210> SEQ ID NO 11
<211> LENGTH: 14
<212> TYPE: PRT
<213> ORGANISM: Escherichia coli

<400> SEQUENCE: 11

Ala Lys Arg Val Ala Pro Glu Leu Leu Gly Gly Pro Ser Gly
1               5                   10
```

SELF-ASSEMBLY MOLECULES

FIELD OF THE INVENTION

The invention relates to self-assembly molecules, and particularly self-assembly molecules useful to form complexes having an affinity to targets of interest.

BACKGROUND OF THE INVENTION

A variety of molecules having affinity for particular binding sites in cells are known. For example, antibodies and cell-surface receptors can bind to specific targets. However, the strength of the interaction between a given molecule and its target will in some instances be low.

Efforts to increase the affinity of antibody fragments to their target have resulted in the production of dimerized antibody fragments, wherein the dimer has two binding sites, each of which is specific for the antibody target. Dimerization has been conducted by a variety of means, generally involving modification of a "tail" region attached to the antibody fragment. Thus, self-associating secondary structures such as helix bundles have been employed in an effort to produce dimerizable units which retain their specificity and ability to bind to a target of interest. However, the use of known self-associating domains can present several problems, including unwanted and non-functional aggregation of the molecules, as well as difficulties in obtaining optimal spacing between molecules, resulting from limits on control over the geometry of the resultant structure. It is often desirable that the binding region of each molecule in a dimer is located on the same face of the dimer, with sufficient spacing between the molecules to allow engagement of their target molecules.

Successful efforts at forming oligomers of more than two self-associating subunits in association with specific-binding regions have been limited. In one instance, a tetramer of subunits comprising a modified helix of the transcription factor GCN4 together with a "miniantibody" was produced. Similarly, the coiled-coil assembly domain of the cartilage oligomeric matrix protein fused to a small peptide has been used to form pentamers. However, the structure of the cartilage oligomeric assembly is believed to be thin and rod-shaped which may render it unsuitable for use with larger peptides or proteins for which greater inter-unit spacing may be needed.

A discussion of efforts to produce self-assembling molecules can be found in Pluckthun et al., 1997, ref. 1, as well as Terskikh et al., 1997 ref. 2.

SUMMARY OF THE INVENTION

Figure 14:
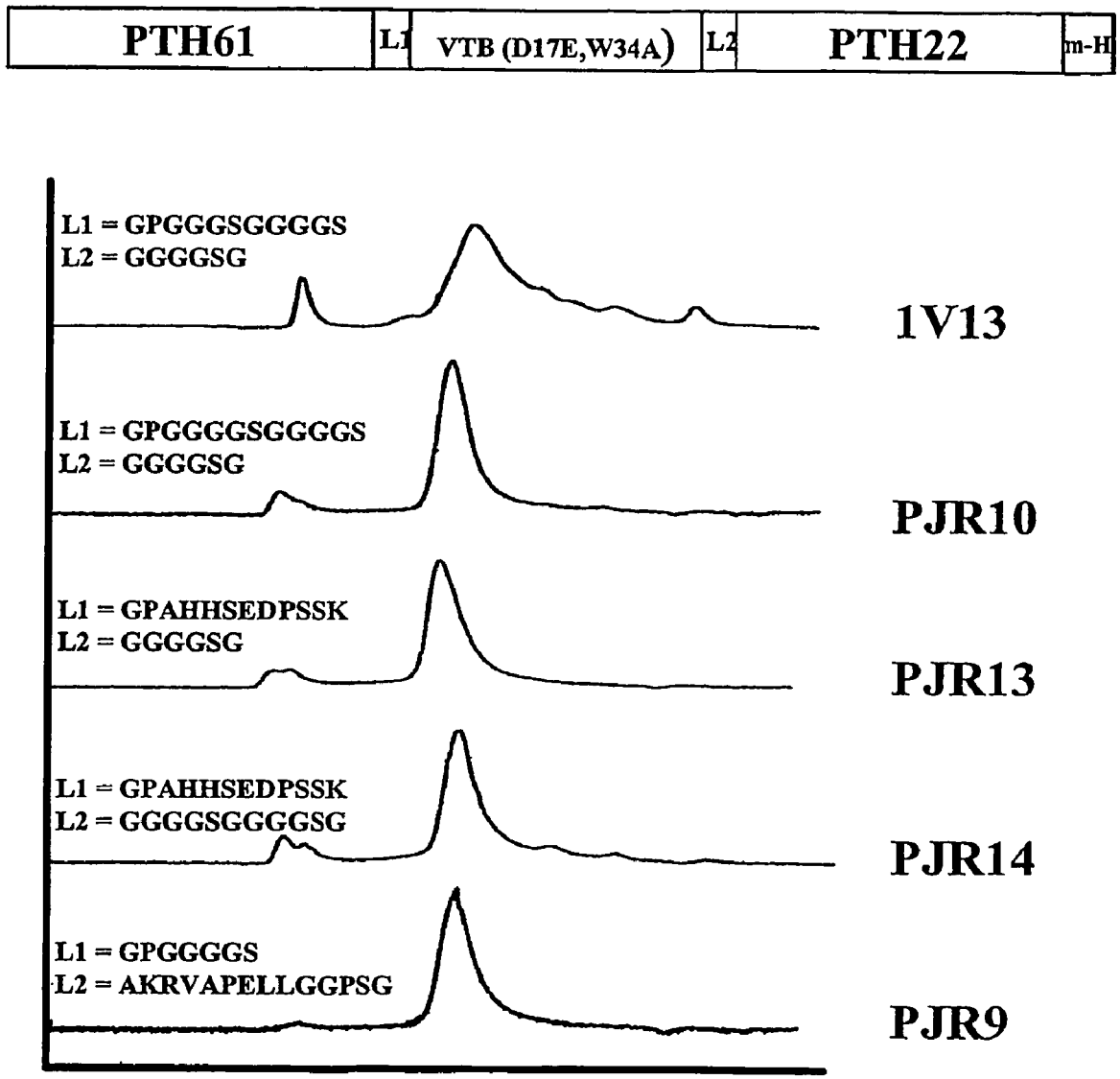

Avidity, the dramatic contribution of multivalency to the strength of biomolecular interactions, is a key feature of antigen-antibody interactions. There is provided herein a method for greatly improving the binding properties of interaction domains such as single domain antibodies (dAbs) through the introduction of avidity. The interaction domains are fused to a suitable self-assembly unit such as the B-subunit of *Escherichia coli* verotoxin ("VTB"). VTB self-assembles to form a homopentamer. When VTB is fused to an interaction domain, the resultant molecules tend to pentamerize. Such pentamerized molecules are referred to as pentabodies.

Introduction of avidity is a very good way of improving the antigen binding properties of antibody fragments. Multimerization is a particularly appealing strategy for the improvement of dAb antigen binding properties.

In an embodiment of the invention there is provided a method of forming a self-assembling multimeric complex, said method comprising obtaining suitable self-assembly molecules, at least three of the self-assembly molecules comprising a complementary self-assembly unit operatively connected to an interaction domain; and combining the self-assembly molecules such that at least three self-assembly units simultaneously bind to one another to form the complex.

In another embodiment of the invention there is provided self-assembly molecules, each comprising a complementary self-assembly unit operatively connected to an interaction domain. More particularly, the present invention provides a self-assembly molecule comprising a plurality of proteinaceous or peptide portions operatively connected together, a first said portion comprising a self-assembly region capable of binding to the self-assembly regions of at least two other self-assembly molecules of the same or different composition, to form a complex of at least three self-assembly molecules, and a second said portion comprising an interaction domain adapted to specifically interact with a target region on another, different molecule.

BRIEF DESCRIPTION OF THE DRAWINGS

These and other advantages of the invention will become apparent upon reading the following detailed description and upon referring to the drawings in which:

FIG. 1 is a depiction of the believed primary structure of an embodiment of the VTB-dAb fusion protein.

FIG. 2 is a ribbon-type depiction of the believed structure of an embodiment of the VTB oligomerization domains in complex with oligosaccharide and with fused dAbs. The saccharide binding face is shown in FIG. 2A, the side view is FIG. 2B, and the believed modeled structure of the embodiment of the PTH50 pentabody is FIG. 2C.

FIG. 3 is a graphical description of the Superdex 200 chromatography and SDS-PAGE results for an embodiment of PTH50-VTB (FIG. 3A), and PTH50 (FIG. 3B). PTH50-VTB fusion product is hereinafter referred to as 1V5, for simplicity.

FIG. 4 is a graphical depiction of the BIACORE analysis of the oligosaccharide binding properties of an embodiment of 2 nM VTB and an embodiment of 2 nM 1V5.

FIG. 5 is a graphical depiction of the BIACORE analysis of the antigen binding properties of PTH50 and an embodiment of 1V5. FIG. 5A relates to binding of 0.25-2 μM PTH50 to immobilized peptide antigen; FIG. 5B relates to the binding of 2-10 μM peptide to immobilized 1V5; and FIG. 5C relates to the binding of 2.5-15 nM 1V5 to immobilized peptide.

FIG. 6 is a depiction of embodiments of certain sequence listings of interest.

FIG. 7 is the heat induced denaturation curve for pentabody 1V5—see Example 1, thermal stability studies.

FIG. 8 shows protease susceptibility of pentameric sdAB—see Example 1, protease stability studies.

FIG. 9 is a diagrammatic presentation of the primary structure of pentabody 1V12, according to Example 2.

FIG. 10 is the result of size exclusion chromatography measurements on iV12.

FIG. 11 is the result of surface plasmon resonance analysis of 1V12 binding.

FIG. 12 is a diagrammatic presentation of the products of Example 3 herein.

FIG. 13 shows the construction and size exclusion chromatography of decavalent single domain antibody 1V13, Example 3 herein.

FIG. 14 is a comparison by size exclusion chromatography of 1V13 and its variations, Example 4 herein.

DETAILED DESCRIPTION OF THE INVENTION

Definitions

As used herein the terms "self-assembly units" and "self-assembling units" refer to peptides or proteins (which may be in association with carbohydrate or other modifications), which are adapted to interact with other such regions on separate molecules to form one or more structures having a substantially defined geometry and including three or more units.

As used herein the term "interaction domains" refer to peptides, or proteins (which may be glycosylated or otherwise modified), which are adapted to specifically interact with target regions (or targets) on other molecules differing from themselves. Preferably the other molecules are not self-assembly units.

As used herein the term "homopentamer" refers to a structure containing five units specifically interacting with one another to form a structure having substantially defined geometry, each unit being substantially identical to the others.

As used herein the term "multimerization" refers to the process by which more than two self-assembling units combine together to form a larger complex of defined geometry.

As used herein "sdAb, and "dAb" refer to single domain antibody fragments.

As used herein the term "complementary self-assembly units" means at least three self-assembly units which are adapted to associate with one another to form a complex having defined geometry.

As used herein the phrase "a structure having substantially defined geometry" means a structure the approximate size and shape of which is consistent when it is formed from the same components under the same conditions.

As used herein the term "derived from genetic material encoding" refers to something which includes a peptide or protein which could have been substantially produced by transcription of DNA and/or translation of RNA encoding that peptide or protein, or a larger protein of which it forms a part, followed if necessary by cleavage (natural or unnatural) and/or post-translational modification. It will be apparent that a peptide or protein will be derived from genetic material even if the actual genetic material encoding it differs through degeneracy in the genetic code or conservative substitution or the like.

Self-Assembly Molecules

The invention provides novel self-assembly molecules (also called "self-assembling molecules" or "subunits") which in one embodiment may comprise a self-assembly unit operatively connected to an interaction domain. Each self-assembly molecule has a portion which under the correct conditions can specifically bind a target and a portion which under the correct conditions can bind to another self-assembly molecule to form a complex of at least three self-assembly molecules. The self-assembly unit may be connected to the interaction domain by a linker region" (also referred to as a "linking region", "linkers", "linking domain" or "linker domain").

It will be readily understood that the self-assembly molecules of the present invention may in some instances be fusion proteins. Such fusion proteins can be synthesized by a variety of means, including chemical synthesis followed by chemical modification as needed, synthesis in bacterial or other culture, or synthesis in a mammalian host, for example through the administration of nucleotides encoding the fusion protein of interest to a mammalian host by gene therapy according to standard techniques. The self-assembly molecules of the present invention can also be produced by any suitable means, including chemical linking of the interaction domain to a region of the self-assembly unit so as to preserve target binding and specificity and self-assembly.

Self-Assembly Unit

The self-assembling unit is defined above. In some instances it will be a protein adapted to form an oligomer of three or more units with similar proteins, such that the resulting structure has a defined geometry.

In some instances it will be desirable to select self-assembling units which assemble so as to substantially orient either their N-terminus or their C-terminus on a single face of the structure. In some instances it will be desirable to select self-assembly units which assemble to substantially align their N-termini on a first face and their C-termini on a second face. In some instances it will be desirable to use self-assembly units which assemble to substantially align a mixture of N-terminal regions and C-terminal regions on a single face of the molecule.

In some instances it will be desirable to use self-assembly units which are not identical to one another. For example, each subunit of the final assembly need not be identical, so long as the binding region of each self-assembling unit is complementary to others, such that three or more self-assembling units can form a complex having a defined geometry.

In some instances it will be desirable to use self-assembling units selected from the self-assembly regions of members of the AB5 toxin family, including but not limited to verotoxin, shiga toxin, heat labile enterotoxin, cholera toxin, and pertussis toxin. In some instances it will be desirable to employ self-assembly units which are, or are derived from, proteins naturally encoded by the same family of organisms as is being used to express the subunits.

In some instances it will be desirable to select self-assembly units which will provide self-assembly molecules which form multimeric structures of 4 to 100 self-assembly molecules. In some instances self-assembly units providing multimeric structures of 5 to 50 self-assembly molecules will be desired, and in some instances, selection to provide multimeric structures of 5 to 15 self-assembly molecules will be desired.

In general, multimeric complexes formed from larger numbers of self-assembly molecules will tend to bind target more strongly than complexes of fewer molecules. However, multimeric complexes which are very large may be less able to pass through matrices or tissues and may be less likely to be taken up by cells.

In some instances it will be desirable to use self-assembling units having a constant of dissociation ("$K_D$" or KD") in the sub-nanomolar range. In some instances it will be desirable to use self-assembling units having a constant of dissociation in the picomolar range.

In some instances it will be desirable to select self-assembling units to provide self-assembly molecules wherein $K_D$ of the interaction of the oligomerization domains is between 10 μM and 1 fM. In some instances a $K_D$ of between 100 nM and 100 fM will be desirable. In some instances a $K_D$ of between 100 nM and 1 pM will be desirable.

In light of the disclosure herein, it is within the capacity of one skilled in the art to determine a suitable $K_D$ and select a suitable self-assembly unit based on the intended application and concentration to be used.

Some self-assembly units, such as verotoxin B-subunit will have a native tendency to bind to a particular cell-surface marker or other target. Where binding to this native target is not desired, it may be disrupted by conventional means, such as mutation of the target binding site while preserving affinity for other self-assembly units.

In one embodiment, the invention provides self-assembly units suitable for use with rather bulky interaction domains, and particularly interaction domains comprising 15 or more amino acids. In another embodiment there is provided self-assembly units suitable for use with interaction domains having 25-500 amino acids. In another embodiment there is provided self-assembly units suitable for use with interaction domains having 50-300 amino acids. In another embodiment there is provided self-assembly units suitable for use with interaction domains having 75-200 amino acids. In another embodiment of the invention there is provided self-assembly units suitable for use with a bulky interaction domain comprising a peptide or protein region which is glycosylated, or has some other modification thereto.

In one embodiment there is provided self-assembly units suitable for use with an interaction domain and a marker. In one embodiment there is provided self-assembly units suitable for use with an interaction domain and a destructive material.

In many instances it will be desired to use self-assembly units which are the smallest which can be used without over-crowding the interaction domains. Over-crowding may result if excessively small self-assembly units draw the interaction domains too close together. In general, self-assembly units which form short squat complexes will generally be preferable to those which form tall slim complexes, as the interaction domains will generally be fused to the same region of each self-assembly molecule, and will therefore frequently appear on the same face. Where long slim self-assembly units are used, the limited space available to the interaction domains on each face may cause interference between them which may reduce the availability of these interaction domains for binding with the target, or may result in the interaction domains being too close together to optimally bind target on the surface.

Without limiting the invention to any particular mechanism or binding region, it is believed that the region of VTB responsible for oligomerization is the beta sheet (AA11-15) and the anti-parallel beta sheet (65-68). These two regions appear to associate on adjacent monomers. Additionally, the circle of five alpha-helices (one from each monomer, AA36-46) appear to play a role in the selective association of these individual self-assembly units with one another. Similar analysis of other self-assembly units, followed by routine testing to confirm the binding site location are possible in light of the present invention, thereby making the identification of significant binding regions possible for a skilled technician.

While this is believed to be the first description of antibody fragment pentamerization, the homopentameric cartilage oligomeric matrix protein has been employed to produce oligomeric peptides termed peptabodies (Terskikh et al., 1997, ref 2). However, with a diameter of approximately 20 Å (Efimov et. al., 1994, ref 3), pentamerization of an antibody fragment with this protein would require a long linker which could result in further complications. A 24 amino acid linker was used for peptide oligomerization. In contrast, a molecular mass of 38.5 kDa the VT B-pentamer is similar in size to the 31.3 kDa matrix protein but has a much different geometry with a diameter of approximately 56 Å. This diameter and the peripheral positions of the N— and C-termini are generally preferable as they allow for presentation of five dAbs without a complicated requirement for long linker sequences.

Thus, self-assembly units may be specifically crafted to provide the geometry, diameter, and N-terminal or C-terminal orientation desired, provided that the regions responsible for association between the self-assembly units, and the geometry, hydrophobicity and charge characteristics necessary for association are preserved.

In light of the disclosure herein, it is within the capacity of a person skilled in the art to identify suitable self-assembly units. While a variety of methods are possible, one reasonable approach is to look at the three-dimensional structure formed when three or more self-assembling units associate, to determine if the C— or N-termini are aligned in a desirable manner, and to identify the spacing between such termini. This information can then be compared to the orientation and space requirements of the desired interaction domain (and linker region, marker and/or destructive material if used) to select suitable self-assembly units. In some instances it will be desirable to select self-assembling units which provide good levels of soluble product when produced from *E. coli*.

Interaction Domains

A variety of interaction domains are contemplated, and will be apparent to one skilled in the art in light of the disclosure herein. For example, interaction domains such as antibodies, antibody fragments, single domain antibody fragments ("dAbs" or "sdAbs"), single chain polypeptides encoding the $V_H$ and the $V_L$ region of an antibody ("scFv"), peptides or proteins derived from the binding region of an antibody, portions of cell surface receptors, the binding region of cell surface receptors, molecules or the binding portion thereof, which specifically bind to cell surface receptors, and other molecules having an affinity for a specific target.

In some instances, such single domain antibody fragments may be produced by isolating antibody fragments from a library encoding antibody variable domains. The size of sdAbs may vary, and can be determined by sequencing the DNA which encodes them.

Single domain antibodies will sometimes be preferable to scFvs for oligomerization purposes. Since they are generally about half the size of scFvs, oligomeric forms of sdAbs are generally much smaller than their scFv counterparts. Also, the yields of soluble product in *E. coli* tend to be much higher for sdAbs than for scFvs. More importantly, however, sdAbs generally exist entirely as monomers whereas scFvs often form dimers, trimers etc. in which the $V_L$ of one scFv associates with the $V_H$ of a second scFv and vice versa. This property can be exploited by carefully choosing the linker length between the $V_L$ and $V_H$ so as to create quite pure dimeric and trimeric scFvs, termed diabodies and triabodies (Hudson et. al., 1999, ref. 4). However, introduction of another layer of oligomerization can also lead to undesired complexity.

It will be apparent in light of the disclosure herein to one skilled in the art that self-assembly molecules recognizing more than one target may also be formed substantially according to the method disclosed herein by linking one interaction domain (such as an sdAb, or the like) to the C-terminal region of a self-assembly unit, and a second interaction domain to the N-terminal region.

When selecting interaction domains, it will frequently be desirable to avoid interaction domains which tend to associate with each other, to the detriment of target binding. Direct binding between interaction domains can not only reduce target binding, but may change the shape of the overall oligomer, and reduce the ability of other interaction domains within the oligomer to bind their target.

The desired constant of dissociation between the interaction domain and its target will depend on several factors, including target abundance, the extent of binding desired, the average and duration of binding desired.

In some instances, an interaction domain will be selected to provide a $K_D$ (for a single, non-oligomerized) self-assembly molecule of between about 1 fM and 100 μM. In some instances a $K_D$ of between about 1 nM and 10 μM will be desired.

In some instances it will be desirable to select an interaction domain and a self-assembly unit to form self-assembly molecules which, in monomer form bind only very weakly to target (e.g. $K_D$ of between about 10 μM to 10 mM, or between about 100 μM to 1 mM), but bind target strongly (e.g. $K_D$ of between about 1 fM to 100 nM or between about 1 pM to 10 nM) in oligomeric form. In this way, a linked toxin or radio-isotope could be targeted to cells expressing the target at high levels, while largely sparing those expressing it at only low levels. This is useful in situations such as some cancers where the abundance of a cell surface marker and not its mere presence, characterizes the undesired cells. A discussion of the use of a different system to provide selective recognition of cells over-expressing a target can be found in Kaminski et al., 1999, ref. 5.

In some instances it may be desirable to select an interaction region or self-assembly unit including a "spoiler". A "spoiler" is anything present on or adjacent or operatively connected to the binding region whereby the binding region is initially unable to bind strongly and is only released from this state upon entry into a cell or tissue type of interest. For example, a change in the accessibility of the binding site could be effected through the action of a tissue-specific phosphatase, such that the dephosphorylated binding site was able to bind effectively whereas in its phosphorylated state it could not.

Similarly, a peptide region which ordinarily blocked a binding site could be selectively cleaved by a tissue-specific protease to enable binding. For example, self-assembly molecules having interaction domains specific for a target found both on prostate cancer cells and on healthy cells in remote tissues could be designed to include a peptide which would ordinarily block the interaction domain binding site for the target on the prostate cancer cell. This peptide could include a sequence sensitive to cleavage by PSA (a prostate-specific protease), such that PSA causes release of the peptide. Thus, the self assembly molecules would not significantly bind target in non-prostate tissue, but would be free to bind cancer cells in the prostate. Where self-assembly molecules include destructive material such as toxins or radio-isotopes, such tissue-specific binding may help to reduce the side effects of cancer therapy.

Linker Region

The connections between a self-assembly unit and an interaction domain may include the use of a "linker region" joining the self-assembly unit and the interaction domain. Linker regions may be selected from any number of peptide sequences or other suitable materials. The length of a linker region will depend on several factors, including the geometry of the self-assembling units, the size of the interaction domain and the size and positioning of a marker or destructive material, if used. It is generally desirable to provide a linker region sufficient to allow the interaction domain operatively connected to each self-assembly unit to orient towards its target, permitting the binding of several interaction domains to their targets when their self-assembly units are engaged to one another.

In some instances it will be desirable to use linkers between four and three hundred amino acids in length, in some instances it will be desirable to use linkers between four amino acids and two hundred amino acids in length, and in some instances it will be desirable to use linkers between five amino acids and twenty amino acids in length. When selecting a linker, it will sometimes be desirable to select a sequence which is resistant to proteases.

In some instances it will be desirable to use linkers of the general formula $(GGGGS)_n$ (n repeats of SEQ. ID. NO. 6), where "n" is preferably between about 1 and 50. It will sometimes be preferable to select "n" to be between 1 and 25, sometimes between 1 and 10 and sometimes between 1 and 4. In some instances a C-terminal linker sequence GGGGS (SEQ. ID. NO. 6) and an N-terminal linker sequence GGGGSGGGGS (double repeat of SEQ. ID. NO. 6) will be desirable.

Linker regions will preferably be selected to allow maximum target accessibility to the binding sites of the interaction domains. Linkers will generally be selected for resistance to proteases where in vivo applications are contemplated. However, there may be instances where linkers with sensitivity to a tissue-specific protease may be employed, for example where a dissociation of the interaction domain from the rest of the complex is desired in a particular tissue.

Linkers may also be used to join a marker (such as biotin, or a radioactive or fluorescently labeled moiety or compound) or a destructive material (such as a toxin or radioactive material of sufficient activity) to a self-assembly unit. In one embodiment, the linker may be secured (for example as a fusion protein) to the opposite terminus of the self-assembly unit from the interaction domain.

Size

The total size of individual self-assembly molecules containing self-assembly units and interaction domains, and linkers (and markers and/or destructive materials) where applicable, will sometimes be of concern. In particular, where the passage of the self-assembly molecule through a matrix or through tissues is desired, smaller self-assembly molecules may be preferable.

In some instances it will be desirable to select subunits to provide a multimeric complex having a diameter between 10 and 200 Å. In some instances a diameter of between 20 and 180 Å will be desirable, in some instances a diameter of between 50 and 150 Å will be desirable. In some instances a diameter of between 60 and 100 Å will be desirable.

It will be readily apparent that the specific embodiments described in detail herein may be conveniently modified to suit other circumstances. For example, the five amino acid sequence present at the N-terminus of the FIG. 1 construct, present only for cloning convenience, can be removed where desired. The ompA sequence is removed during secretion of the mature protein to the $E.\ coli$ periplasm. The $His_5$ tails will not always be required as an affinity purification method based on the fusion protein's retention of the $P^k$ trisaccharide binding of VTB (FIG. 4) could be applied instead. Given the availability of anti-VTB monoclonal antibodies (see Soltyk et. al., 2002, ref. 6), the c-myc detection tags will not always be necessary. (Together these modifications would reduce the size of the pentavalent molecule by 13.5 kDa.)

Variations, modifications and alternative embodiments are specifically contemplated and will be apparent to one skilled in the art in light of the disclosure herein.

Internalization In some instances it will be desirable to select self-assembly units, interaction domains (and where needed linkers, markers and/or destructive material) to provide self-assembly molecules which are capable of being internalized into cells in their monomer form. In some instances it will be desirable to design self-assembly molecules such that multimeric complexes are readily internalized into cells.

Specific triggers for internalization of bound molecules are known. For example, mechanisms for the internalization of materials bound to certain cell surface receptors are known. Thus, in light of the disclosure herein, it is within the capacity of a technician skilled in the art to produce a subunit suitable for internalization in a particular cell type in monomer or oligomer form. Internalization may be desirable, for example, where the subunits include types of toxins or radioisotopes which preferentially act from within the cell.

Diagnostic Use

The self-assembly molecules and multimeric complexes of the present invention are useful for the diagnosis of conditions, as well as the identification of proteins and other materials of interest in biological material. For example, an interaction domain specific for a tumour antigen may be fused to a suitable self-assembly unit and to a radioactive or chemically recognizable marker subunit to provide self-assembly molecules having diagnostic applications. For example, self-assembly molecules of this type will tend to form multimeric complexes in regions where the antigen is found at high levels on a surface, such as a tumour cell. The presence of the multimeric complex can be determined through identification of the marker and can be used to diagnose the presence of tumour cells either in culture, or within an individual. Similarly, subunits containing interaction domains specific for known pathogens in food, water, or similar materials can be used to assay the safety of samples of these products.

The formation of the multimeric complex may improve the avidity of binding to target, thereby improving the sensitivity of these assays, as well as providing for a stronger signal strength, making identification of contaminated products easier.

Therapeutic Use

The self-assembly molecules and multimeric complexes of the present invention may be used in the therapy of a number of conditions in mammalian subjects. Self-assembly molecules having an interaction domain specific for a marker of a cell type of particular interest (or specific for a marker which is more highly expressed on a cell type of particular interest, such that binding of the subunit to the cell type of interest will occur preferentially to binding to other cell types) may be employed for therapeutic use.

Where it is desired to destroy a particular cell type, a toxic or otherwise destructive "payload" may be added to the subunit. For example, where the self-assembly unit is the verotoxin B-subunit, or a variation thereof, it may be desirable to include the verotoxin A-subunit as well. Verotoxin B-subunit will ordinarily be modified to eliminate or substantially reduce its inherent binding to the $P_K$ antigen. The verotoxin A-subunit is toxic, and when added to a subunit specific for an undesired cell type, can be used to eliminate cells of that type within a patient, or within a culture of patient cells destined for re-administration to the patient.

For example, the VEGF receptor is overexpressed in the vasculature of many tumour types. Thus, the destruction of cells over expressing this receptor could be used to compromise blood flow to tumours, thereby potentially reducing tumour load and improving therapeutic outcome. Similarly, HER-2 is overexpressed in many breast cancers and would be a suitable target in order to reduce the load of breast cancer tumour cells in a subject. Interaction domains specific for particular cell surface targets may be readily identified, once the target itself is known. In many instances an sdAb specific for cell surface targets will be the preferred interaction domain.

In some instances it will be desirable to use multimeric complexes to bring two different cell types into close proximity. For example, it may be desirable to bring a killer cell to an undesired cell type, such as a cancer cell. This may be readily accomplished in light of the present disclosure by forming a multivalent molecule which displays an interaction domain specific for the undesired cell type on one face and an interaction domain specific for the killer cell on the other face. For example, a decavalent molecule displaying an sdAb recognizing the cancer cell on the C-terminal face of VTB and having a second sdAb which recognized the killer cell on the N-terminal face of VTB would allow the killer cell and tumour cell to be brought together, facilitating destruction of the cancer cell.

In light of the disclosure herein and the position of the N-terminus and C-terminus (FIGS. 2A and 2B), it is within the capacity of a skilled technician to generate such decavalent structures.

When used with respect to therapeutic treatments and compositions, the term "effective amount" refers to an amount which, when administered to the patient over a two-week period causes a significant reduction in the number or viability of the undesired or over-expressed cell or substance.

In some instances, multivalent-bispecific antibodies will have advantages over bivalent-bispecific antibodies, particularly where there is multivalent antigen presentation, such as on cell surfaces.

The oligomerization strategy described here, particularly when used in conjunction with phage display techniques, provides a relatively rapid means of isolating antibody reagents for use in proteomics. Furthermore, immunotoxins in which interaction domains are fused to a destructive material or toxin such as the highly toxic VTA subunit or incorporate or are bound to a radioisotope can be produced in light of the disclosure herein, and such immunotoxins may provide for wide-ranging therapeutic and diagnostic uses.

In some instances it will be desirable to use non-identical self-assembly molecules. The individual self-assembly units will still preferably specifically recognize one another, enabling the formation of a multimer of predictable geometry and size. However, one or both of the interaction domain or the self-assembly unit will differ between the molecules.

For example, it may be desirable to express several different interaction domains and have them come together in multimeric complexes. This could be accomplished by producing various fusion proteins having the same self-assembly unit and a different interaction domain. Alternatively, and particularly where it is desired to maintain a certain stoichiometry between the different interaction domains, it may be desirable to use different self-assembly units which nonetheless assemble together to form a multimeric complex of known geometry and size. For example, pertussis toxin is a heteropentameric product, containing four different B-subunits, one of which is present in duplicate. Thus, if it was desired to form a pentamer having four different interaction domains, one of which was present in two copies in the pentamer whereas the other were only present in a single copy, this could be accomplished by forming four different fusion proteins corresponding to the four different B-subunits of pertussis toxin, with each subunit being fused (through a suitable linker domain if needed) to a different interaction domain. Such an assembly could be particularly useful in cases where several different target molecules are expressed in very close proximity to one another, and it is their co-expression, or their close relation to one another which is particularly indicative of the cell type of interest.

EXAMPLE 1

Summary

In one embodiment of the invention there is provided a novel procedure to improve the avidity of interaction domains by fusing the antibody fragment to the C-terminus of the verotoxin B-subunit. This generates pentameric sdAbs, termed pentabodies. The pentabody described here bound immobilized antigen 7,000 fold more strongly than the monomeric sdAb. This technology can be easily applied to other sdAbs, single chain variable fragments, as well as other suitable interaction domains. Antigen binding affinities can also be improved by in vitro affinity maturation (refs. 7 and 8) although this is a time consuming process that involves the construction of and panning of sub-libraries. In some instances in vitro affinity improvement may modify fine-specificity or introduce unwanted cross-reactivity (ref. 9).

In the instance of an sdAb specific for a peptide antigen, pentamerization resulted in a 7,000-fold increase in functional affinity for immobilized antigen. The pentavalent sdAb was expressed in high yield in Escherichia coli and displayed excellent physical properties. This technology in conjunction with phage display techniques provides a rapid means of generating novel antigen binding molecules with subnanomolar affinities for immobilized antigen. While phage display frequently offers a more efficient means of isolating monoclonal antibodies than hybridoma technologies (ref. 10), the dissociation constants of antibody fragments isolated by phage techniques are typically in the $10^{-5}$ to $10^{-7}$ $M^{-1}$ range (refs 11 and 12) and may be too low for many applications.

Single domain antibodies are typically based on the variable domains of heavy chain antibodies whose variable domains have excellent physical properties that relate to their natural existence in absence of a light chain partner. One useful source of antibodies is a single domain antibody library, derived from the llama heavy chain antibody repertoire and displayed on phage [Tanha (2001), ref. 13]. This library was the source of the antibody selected for evaluation of the oligomerization strategy described here.

The verotoxin B-subunit monomer ("VTB") was chosen as a non-limiting example of a self-assembly domain because of its relatively small size and the structure of the homopentamer that it forms by self-assembly. The verotoxin B-pentamer has a doughnut-shaped structure with the N— and C-termini exposed on opposite sides of and at the periphery of the molecule.

Verotoxin, or shiga-like toxin, is an $AB_5$ toxin in which the A subunit is the toxic entity and the pentameric B-subunit mediates binding to the glycolipid globotriaosylceramide, abbreviated $Gb_3$, (Gal$\alpha$1→4Gal$\beta$1→4Glc$\beta$1→ceramide). Native E. coli verotoxin subunit B binds to eukaryotic cell membranes via the glycolipid $Gb_3$ receptors. Verotoxin has several varieties. Specific work reported herein was conducted with VT-1, although the process is believed equally applicable to other varieties, and such are within the scope of the invention.

It is possible to overcome $Gb_3$ binding by mutation of VTB. For example, the W→A mutation of amino acid 34, combined with either a D17E mutation or a A56Y mutation abolish detectable binding to glycolipid (Soltyk, et al., Ref. 6). Thus, it is within the capacity of one skilled in the art in light of the disclosure herein to prepare VTB mutants which do not significantly bind $Gb_3$.

For purposes of illustrating the full potential of a pentavalent sdAb in terms of binding to an immobilized or cell surface antigen, an sdAb recognizing a relatively small antigen that could be immobilized at quite high density was chosen. Accordingly, an sdAb specific for a modified 31 amino acid peptide sequence from human parathyroid hormone ("PTH50") was isolated from a llama sdAb library (ref. 13) by phage display. The peptide has the sequence $^1$SVSEIQLMHNLGKHLNSMERVEWLRKLLQDV$^{31}$ (SEQ. ID. NO. 1) with a β-lactam bond linking the side chains of $^{22}$E and $^{26}$K (shown in bold). The anti-PTH sdAb (PTH50) expressed extremely well in E. coli (approximately 200 mg/L) and did not aggregate.

Figure 2A:
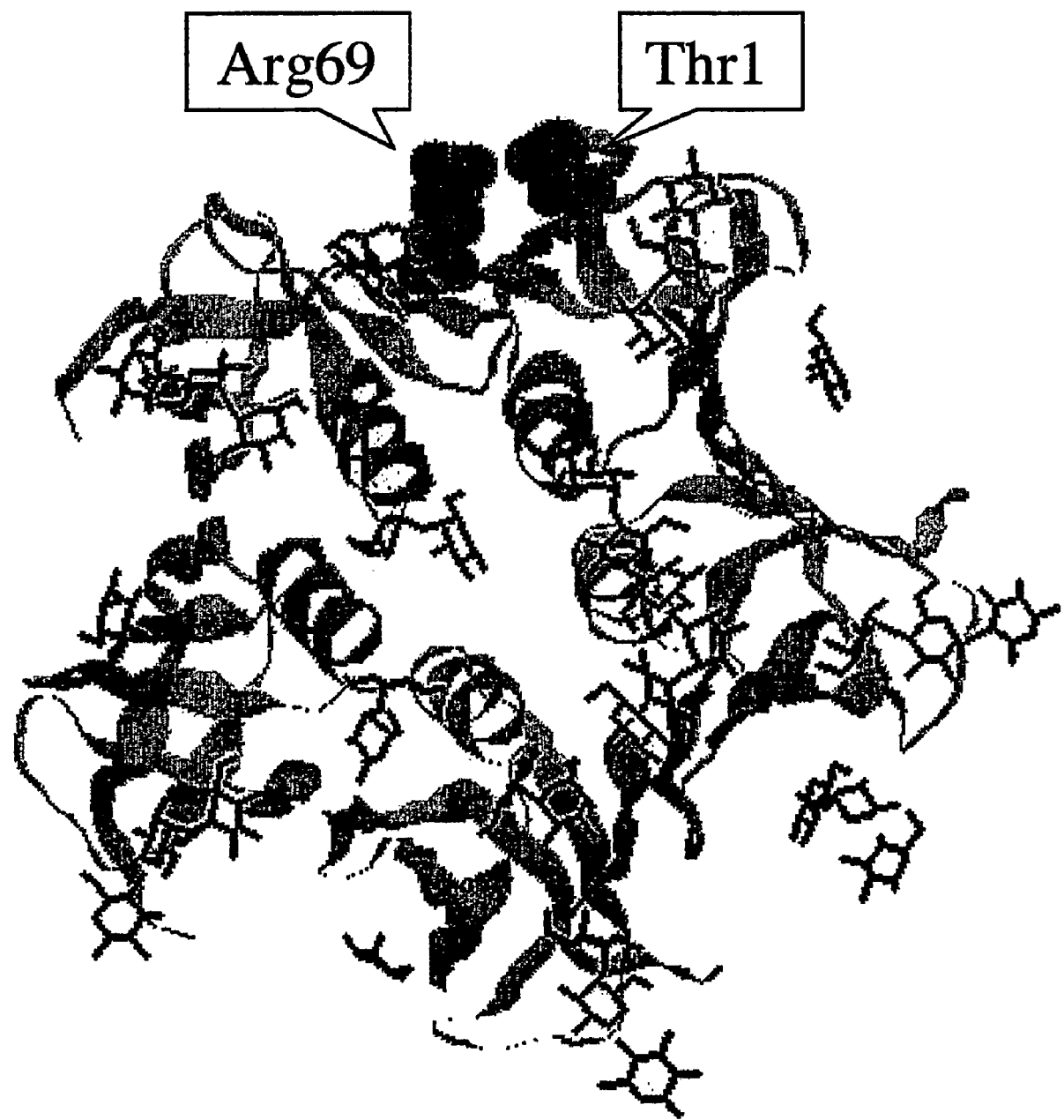
Figure 2B:
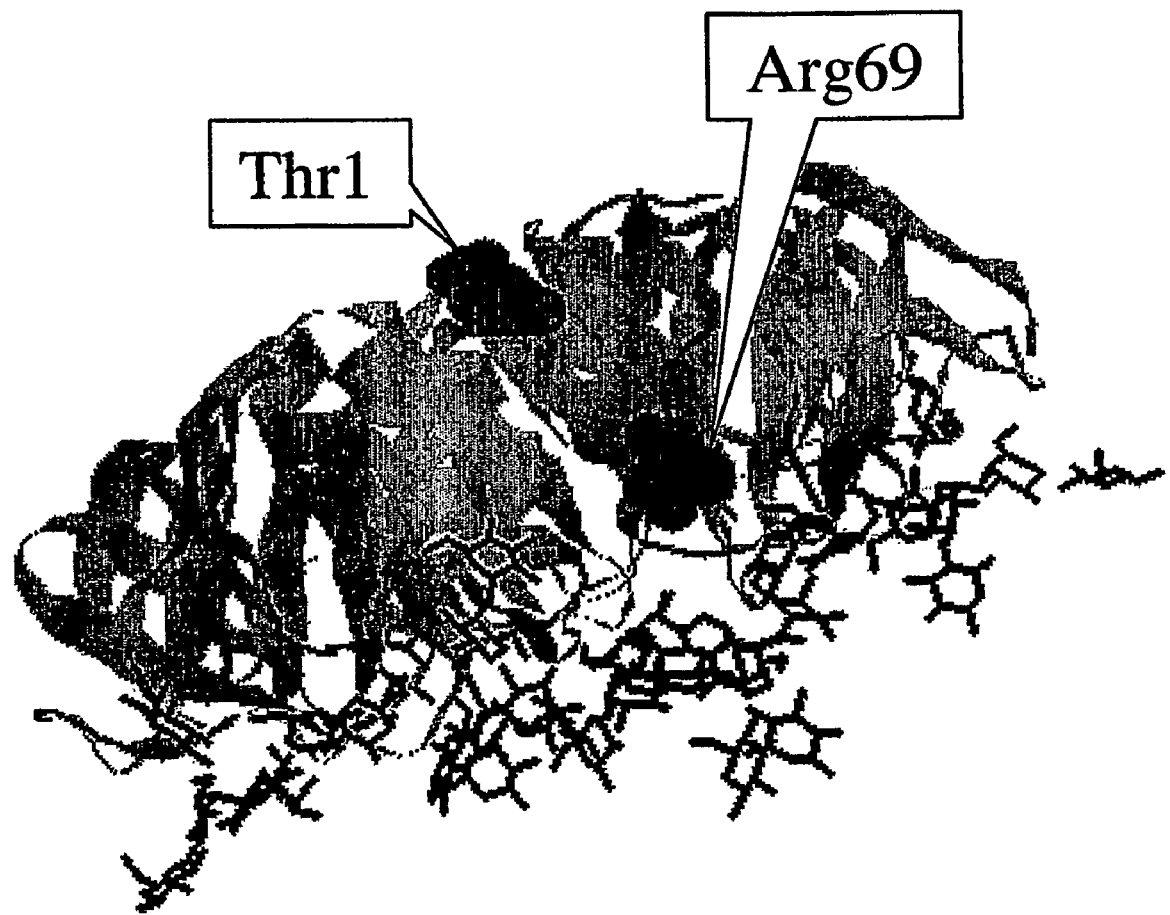

The anti-PTH sdAb was fused to VT B-subunit monomer as diagrammed in FIG. 1. The dAb was fused to the VTB C-terminus so as to position the sdAbs away from the oligosaccharide binding sites of the B-pentamer since retention of carbohydrate binding activity provides a convenient means of fusion protein purification by affinity chromatography (FIG. 2A). For cloning convenience arising from the presence of a PstI restriction site near the 5'-end of the sdAb gene, the VTB gene was inserted after sdAb residue 5, which placed five amino acid N-terminal extensions on the B-pentamer. The five displaced sdAb amino acids were replaced in the sdAb, which was fused to the VTB by a five amino acid spacer and followed by detection and purification tags.

A modeled structure of the pentabody (FIG. 2C) shows the five sdAbs radiating out from the C-terminal side and periphery of the VTB core. The highly symmetric representation of the pentabody is considered to be a snapshot of a highly dynamic structure. The sdAbs are thought to be highly flexible since modeling the fusion PTH50 to VTB via linker 2 without molecular overlaps in space was relatively easy.

Figure 3:
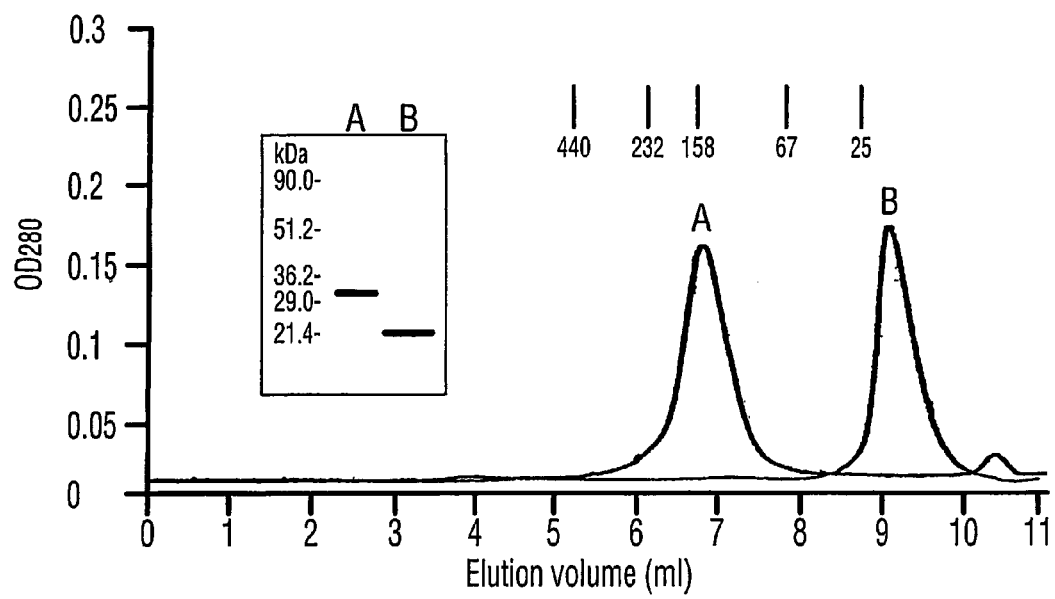

Size exclusion chromatographic analyses showed that both PTH50 and 1V5 were very homogeneous with respect to oligomerization state. This is shown FIG. 3, SPERDEX 200 chromatography and SDS PAGE (12%) of an embodiment of 1V5 (A) and PTH50 (B). Based on the molecular mass markers separated under the same conditions, the mass of 1V5 was estimated to be 128 kDa, which is very close to the predicted size of 114.5 kDa for the pentameric fusion protein.

Figure 4:
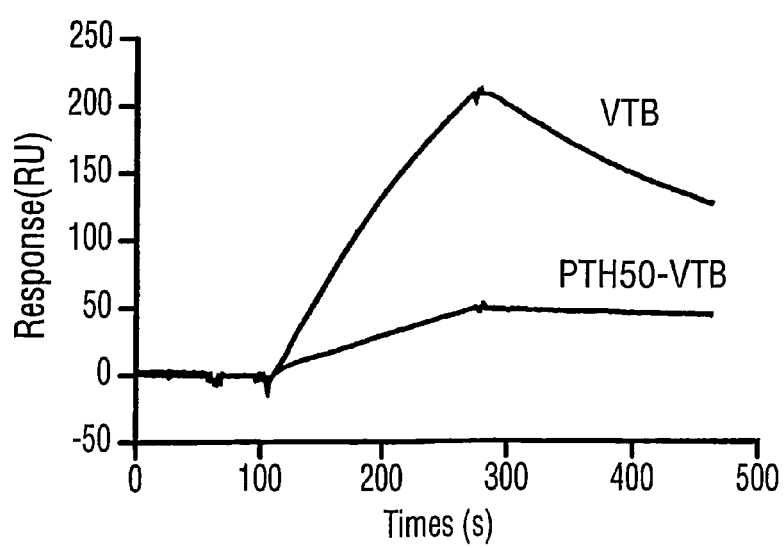

Retention of the full saccharide binding activity of VTB by 1V5 confirmed that the fusion protein was pentameric. The crystal structure of VTB in complex with a Globotriaosylceramide, Gal-alpha(1-4) Gal-beta(1-4) Glc-betal-ceramide ("$Gb_3$") analogue (ref. 14) shows the presence of fifteen $Gb_3$ trisacharides, also known as the $P^k$ trisaccharide, per VTB pentamer (FIG. 2A). SDS-PAGE showed that while 5 μM PTH50 did not bind to the Synsorb $P^k$ resin, the vast majority of 1V5 did bind at this concentration. At this concentration the pentameric structure is required for effective oligosaccharide binding (ref. 6). Somewhat surprisingly, surface plasmon resonance ("SPR") data showed that the $K_D$ of the 1V5 trisaccharide interaction was approximately 1.7 nM compared to 6.6 nM for the VTB saccharide interaction. Possibly the five amino acid N-terminal extension on IV5 (FIG. 1) interacts with the spacer on the neoglycoconjugate, resulting improved binding of the fusion protein to trisaccharide, relative to VTB. In any case, the data are consistent with the formation of a fully functional pentameric molecule. FIG. 4 presents the BIACORE analysis of an embodiment of the oligosaccharide binding properties of 2 nM VTB and 2 nM 1V5. Fitting of the data to a 1:1 interaction model gave $k_a$s of $2.6 \times 10^6$ $M^{-1}s^{-1}$ and $5.1\times10^5$ $M^{-1}s^{-1}$ for VTB and 1V5, respectively, and $k_d$s of $1\times10^{-2}$ and $8.8\times10^{-4}$ for VTB and 1V5, respectively.

Figure 5:
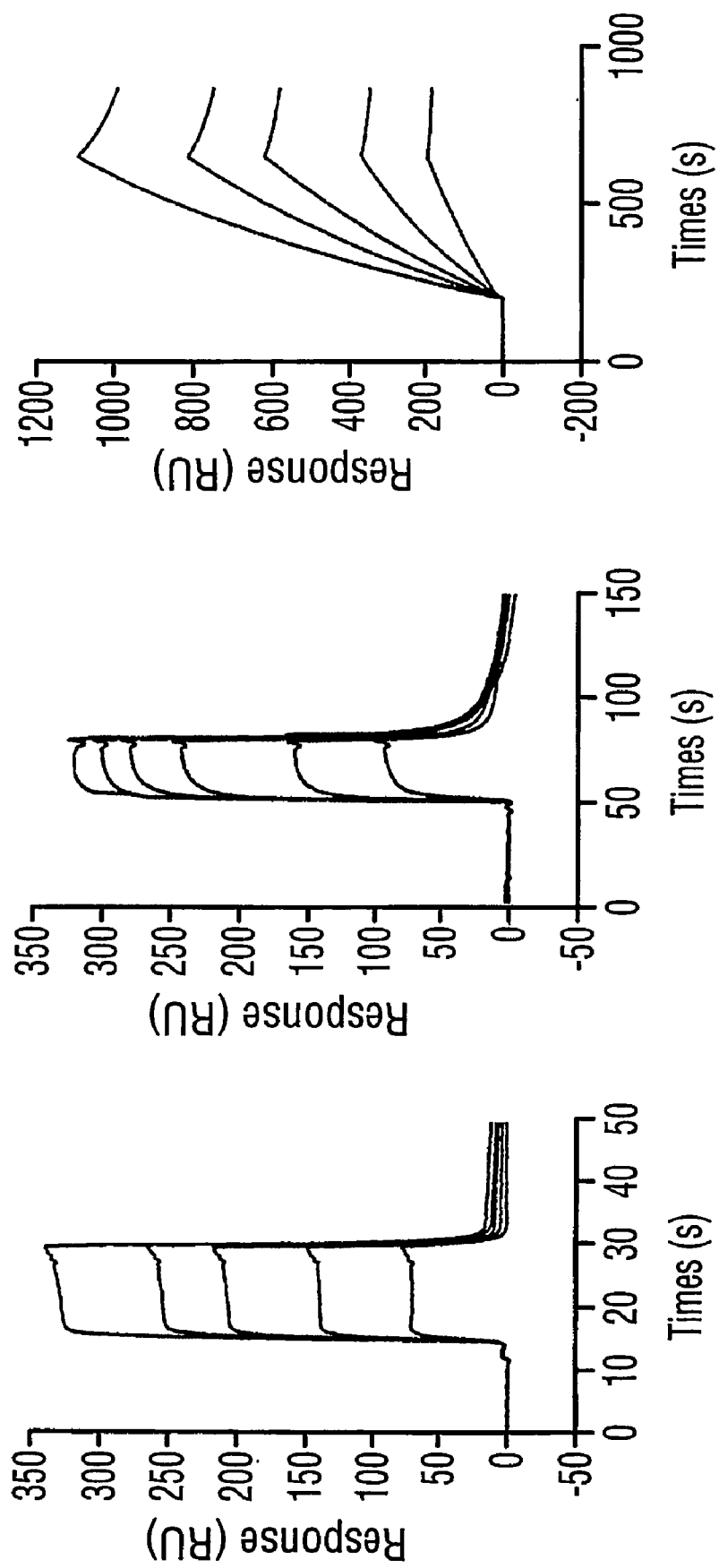

The antigen binding profiles of PTH50 and 1V5 confirmed that the VTB fusion protein bound immobilized peptide much more effectively than the monomeric sdAb (FIG. 5 and Table 1). PTH50 binding to immobilized peptide (FIG. 5A) displayed rapid but analyzable kinetics. The $K_D$ of the interaction was determined to be 2.5 µM (Table 1). Although rate constants could not be derived for the interaction of peptide with immobilized pentabody (FIG. 5B), the $K_D$ was determined to be 3.6 µM (Table 1) indicating that pentamerization did not significantly alter dAb binding site accessibility. The binding of 1V5 to immobilized peptide was analyzed at low concentrations in order to maximize the binding valency and assess avidity gain conferred by dAb pentavalency (FIG. 5C). Under these conditions of antigen surplus, the pentavalency conferred an avidity gain of approximately 7,000 (Table 1). FIG. 5 presents BIACORE analysis of an embodiment of the antigen binding properties of an embodiment of PTH50 and 1V5. (A)—binding of 0.25-2 µM PTH50 to immobilized peptide antigen; (B)—binding of 2-10 µM peptide to immobilized 1V5 and (c)—binding of 2.5-15 nM 1V5 to immobilized peptide.

BIACORE analysis was carried out according to standard procedures using CM5 sensor chips. Results as shown in FIGS. 4 and 5 show response units (RU) on the y axis. 1RU is a result of $pg/mm^2$ of protein binding to the immobilized ligand.

Detail of Example 1

Isolation of PTH50. The PTH50 sdAb was isolated from a non-immunized llama dAb library constructed as described elsewhere (ref. 13). Panning was performed with 100 µg of streptavidin-coated paramagnetic particles (SA-PMPs) (Promega, Madison, Wis.) that had been washed according to the manufacturer's instructions. Tubes were shaken frequently to maintain the SA-PMPs in suspension during all steps involving SA-PMPs. To reduce background binding, the library phage were pre-incubated in the absence of antigen with SA-PMPs that had been blocked with 100 µl 2% milk in phosphate buffered saline (MPBS) for 1 hr at room temperature. Also, the SA-PMPs used in panning were blocked in 400 µl MPBS at 37° C. for 2 hr. The panning mixtures contained pre-adsorbed phage ($10^{12}$ tu in the first round and $10^{11}$ tu in subsequent rounds), 20 mg/ml BSA, 0.05% TWEEN™ 20 and 1 µg/ml biotinylated antigen in a total volume of 150 µl MPBS. The phage-biotinylated antigen complexes were captured by transferring the mixtures to tubes containing blocked SA-PMPs followed by incubation at room temperature for 30 min. The SA-PMPs were washed five times with PBS containing 0.05% Tween-20 and then five times with PBS. Bound phage were eluted and propagated on agarose top plates as described (ref. 13). After overnight incubation at 37° C. the phage particles were eluted from the plates, purified and tittered (ref. 13).

Screening of phage clones for antigen binding activity was performed by ELISA as described by Tanha et al. (ref. 13). Biotinylated peptide, 1 µg/ml, was captured at room temperature for 30 min in wells that had been blocked for 2 h with MPBS at 37° C. following overnight coating with 5 µg/ml streptavidin at 4° C. In control experiments biotinylated antigen was replaced with appropriate buffer. Several peptide specific antibodies were identified[4], one of which, PTH50, was selected for this study.

Construction of VTB-PTH50. Standard cloning techniques (ref. 15) were used to generate the VTB-PTH50 or 1V5 gene (FIG. 1). The VTB gene (Accession EMBL M16625) was amplified by PCR with primers that introduced PstI sites at both ends and added a sequence encoding DVQLQ (SEQ. ID. NO. 3) at the C-terminus of VTB. The PCR product was digested by PstI and ligated into the PTH50 gene (GenBank AF447918) linearized with the same enzyme. The PstI site encodes residues 5 and 6 of PTH50 (FIG. 1) and hence the DVQLQ C-terminal extension (SEQ. ID. NO. 3) on the VTB PCR product. A clone in which VTB was inserted in the correct orientation was identified and designated clone pJR1V5.

Molecular modeling. The structure of 1V5 (SEQ; ID. NO. 2) was modeled using the BIOPOLYMER™ and DISCOVERY 3™ modules of INSIGHT II™ on a R10,000 SGI workstation. The PTH50 model is SEQ. ID. NO. 4 (protein) and SEQ. ID. NO. 5 (DNA). The spacers were constructed using the Insight II amino acid database. Potentials were fixed using the AMBER force field and energy minimizations were performed at all steps of the model building.

Expression and purification. *Escherichia coli* TG1 and ER2537 (New England Biolabs) harboring plasmids encoding PTH50, and PTH50-VTB were cultured and induced with 1 mM isopropyl-β-D-thiogalactopyranoside. Periplasmic proteins were extracted by osmotic shock substantially according to the method of Skerra et al. 1991—ref. 16 and the recombinant proteins were purified by immobilized metal affinity chromatography (IMAC) (HI-TRAP™, Amersham Pharmacia). Purifications were monitored by Western blotting with an anti-c-myc monoclonal antibody and an anti-mouse IgG/alkaline phosphatase conjugate. The purified proteins were concentrated by CENTRICON 10™ ultrafiltration (AMICON™), dialysed against 10 mM HEPES, pH 7.4, containing 150 mM NaCl and 3.4 mM EDTA and analyzed by SDS-PAGE.

Size exclusion chromatography. The oligomerization states of PTH50 and 1V5 were assessed by SUPERDEX 200™ (Amersham Pharmacia) size exclusion chromatography. In both instances separations were carried out in 10 mM HEPES, pH 7.4, containing 150 mM NaCl, 3.4 mM EDTA and 0.05% TWEEN 20™.

Oligosaccharide and antigen binding activities. To determine if 1V5 retained the oligosaccharide binding activity of VTB and if this activity could be exploited for dAb-VTB fusion protein purification 5 μM PTH50-VTB, as well as 5 μM PTH50, were mixed with SYNSORB $P^k$™, a resin comprised of the $P^k$ trisaccharide immobilized on CHROMOSORB P™. The binding of the two proteins to the resin was monitored by SDS-PAGE. The oligosaccharide binding activities of VTB and PTH50-VTB were compared by surface plasmon resonance (SPR). Analyses were performed with a BIACORE 3000™ biosensor system (Johnson) (Biacore, Inc., Piscataway, N.J.) on proteins that were purified by size exclusion chromatography as described above. A neoglycoconjugate, BSA-(spacer-O-Galα1-4Galβ1-4Glcβ)$_n$ (Glycorex AB), was immobilized, at a surface density of 13,000 RUs, on research grade CM5™ sensor chips (Biacore, Inc.) at a concentration of 100 μg/ml in 10 mM acetate, pH 4.5. by amine coupling according to the manufacturer's instructions. Analyses were carried out at 25° C. in 10 mM HEPES, pH 7.4, containing 150 mM NaCl, 3 mM EDTA and 0.005% P-20 at a flow rate of 10 μl per minute. The surface was regenerated by contact with 100 mM HCl for 3 s.

The antigen binding profiles of PTH50 and 1V5 were analyzed by SPR. Peptide antigen and 1V5 were immobilized at surface densities of 1,300 RU and 6,000 RU, respectively, on research grade CM5 sensor chips by amine coupling and according to the manufacturer's instructions. Immobilizations were carried out at protein or peptide concentrations of 50 μg/ml in 10 mM acetate, pH 4.5. Analyses and data analyses were performed as described above. Regeneration was not required with the 1V5 surface. The peptide surface was regenerated by contact with 10 mM borate, pH8.5, containing 1M NaCl and 0.1% P-20 for 30 s. Data were evaluated with the BIAEVALUATION 3.0™ software from Biacore, Inc. Kinetics and affinity results are shown in the following Table 1.

TABLE 1

Kinetics and affinities of PTH50 and 1V5 binding to peptide antigen.

| Ligand | Analyte | $k_a(M^{-1}s^{-1})^a$ | $k_d(s^{-1})^a$ | $K_D(M)$ | Relative $K_D$ |
|---|---|---|---|---|---|
| Peptide | PTH50 | — | — | $7 \times 10^{-6b}$ | 1 |
| VT1B-PTH50 | peptide | — | — | $4 \times 10^{-6b}$ | 0.6 |
| peptide | 1V5 | $3 \times 10^5$ | $3 \times 10^{-4}$ | $1 \times 10^{-9}$ | 0.00014 |

Figure 7:
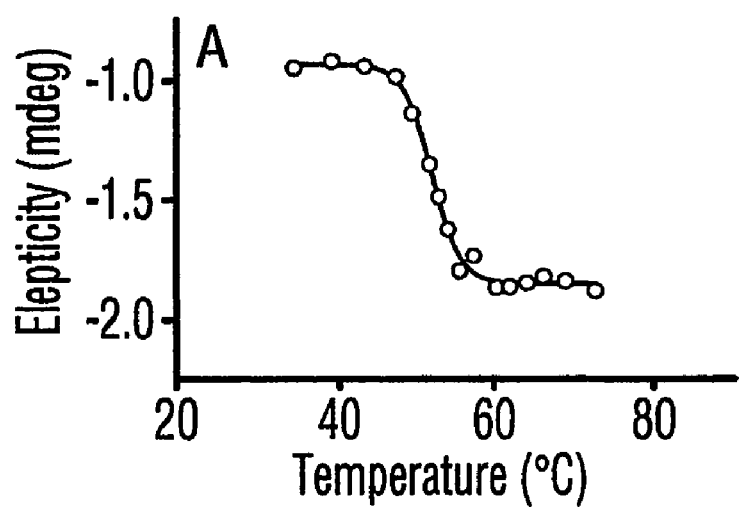

$^a$Rate constants derived by data fitting to a 1:1 interaction model
$^b$Determined by Scatchard analysis because the kinetics were too rapid for determination of rate constants Thermal Stability of VTB-PTH 50 and its Building Blocks For the determination of thermal stability of the pentabody 1V5, circular dichroism (CD) spectra of 1V5 as well as its building blocks, PTH50 sdAb and the VT1B pentamer, were measured at various temperatures. Circular dichroism (CD) spectra were recorded with a Jasco J-600 spectropolarimeter connected to Neslab RTE-110 water bath. Experiments were performed in 10 mM sodium phosphate buffer pH 7.0 using circular cuvettes with pathlengths of 5 cm (for PTH50 and VT1B at concentrations of 1.8 and 3 μg/ml, respectively) and 1 cm (for 1V5 at a concentration of 9 μg/ml). Spectra were recorded from 215-260 nm at 0.2 nm intervals, a scan speed of 20 nm per min, a bandwidth of 2 nm and an integration time of 1 s. Protein spectra were subtracted from a blank spectrum and subsequently smoothed by Jasco software. To determine $T_m$s, sample temperatures were gradually increased from 30° C. to 82° C. Spectra were recorded at various temperatures following a 10 min temperature equilibration time. An average of five elepticity values at 235, 234.8, 234.6, 234.4 and 234.2 nm was used to plot the sigmoidal graph of elepticity versus temperature and $T_m$s determined as the temperature corresponding to 50% unfolding—see FIG. 7.

The data collected at 234.2, 234.4, 234.6, 234.8 and 235 nm were used to obtain denaturing curves for the proteins. No obvious changes in the CD spectra of VT1B were observed, even at temperatures as high as 70° C. Above 72° C., a sharp increase in signal was observed because of protein precipitation (data not shown). This result indicates that the VT1B pentamer is a very stable structure although a $T_m$ could not be determined. The abrupt loss of solubility at high temperature without any indication of denaturation suggests that maintenance of the structure is dependent on pentamer formation. The melting temperature of PTH50 spans a relatively wide temperature range, which is typical of non-cooperative conformational change and frequently observed with small peptides. The melting temperature was calculated to be 59.7 C, indicating that the protein has very good thermostability. The fusion protein made of the two building blocks has a typical heat-denaturation curve with a $T_m$ of 52 C (FIG. 7, the heat-induced denaturation curve for pentabody 1V5). Although this number is lower than the $T_m$ of PTH50 the fusion protein is. less thermostable than VT1B, 1V5 is nonetheless a very heat stable molecule.

The thermal stability of the pentabody described here is a good indicator for use of these molecules in various applications. While high thermostability is always a useful property it is very important for in vivo medical applications. Despite high antigen binding affinity, a tumor-specific scFv failed to localize in xenographs because of its insufficient thermal stability (Willuda et al., 1999, ref 17). Grafting the antigen binding loops of the tumor-specific scFv onto the framework of a highly stable scFv produced a molecule with good serum stability and tumor localization.

Protease Stability of Pentabodies

Tryptic and chymotryptic digestion experiments were carried out at enzyme:pentameric sdAb ratio of 1:200 for 1 h at 37° C. using sequencing grade trypsin and chymotrypsin purchased from Boehringer Mannheim. Digestion mixtures contained approximately 2 μg/ml of 1V5 in 100 mM Tris-HCl buffer, pH 7.8. The chymotrypsin digestion mixture was supplemented with 50 mM $CaCl_2$. The reactions were terminated by adding 10 μl of 0.1 μg/ml trypsin-chymotrypsin inhibitor (Sigma). For molecular weight determinations by mass spectrometry, DTT was added to a final concentration of 200 mM and the samples were processed as described previously by Tanha, J. et al, ref 18).

Figure 8:
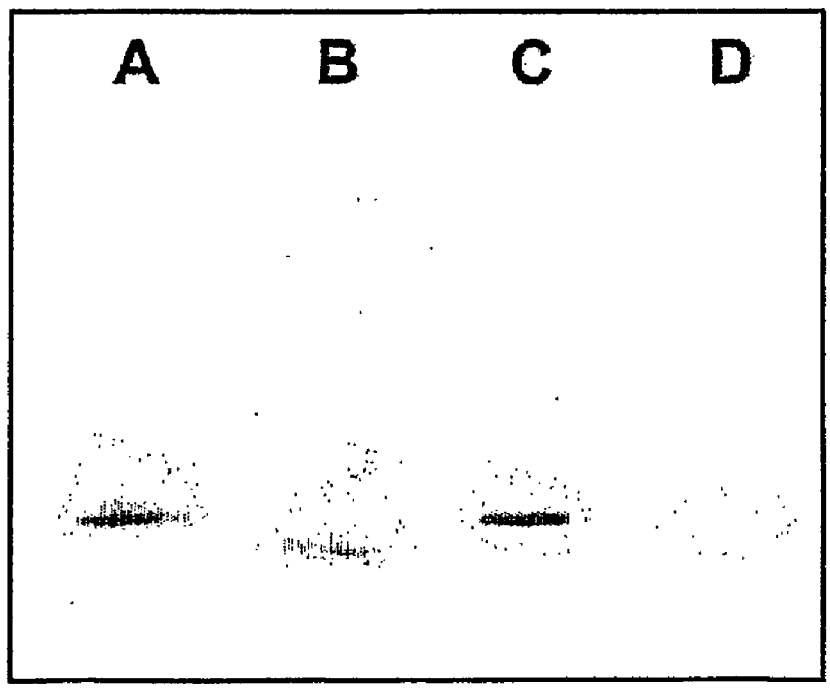
Figure 12:
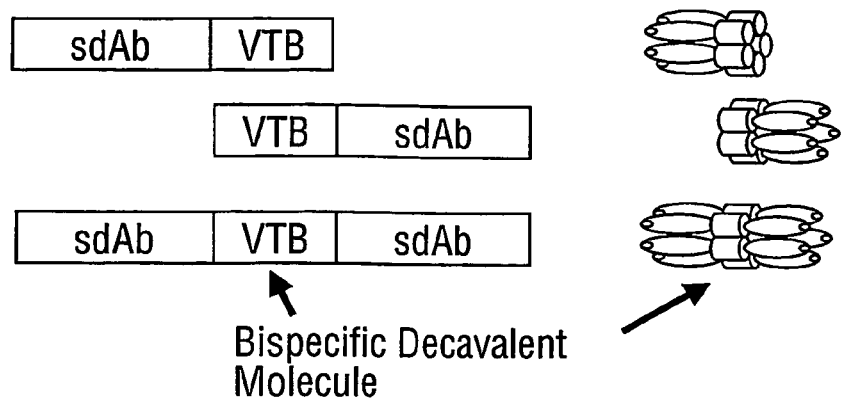
Figure 13:
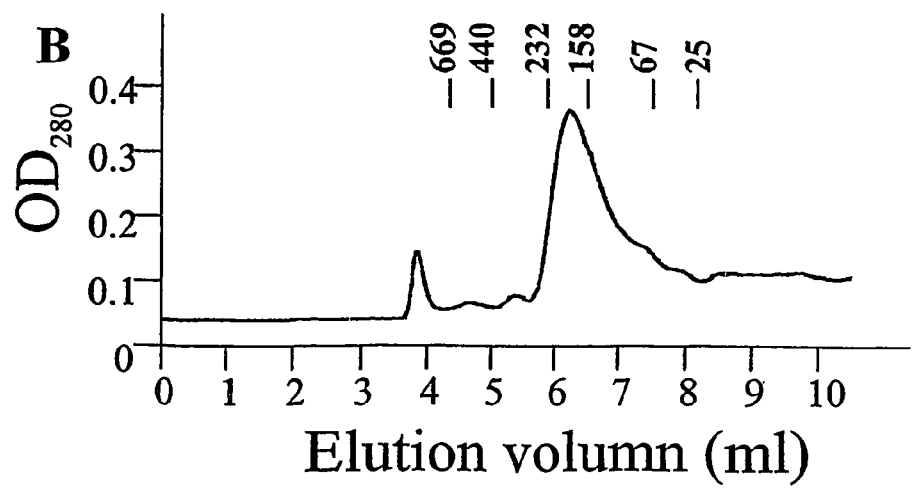

FIG. 8 shows the protease susceptibility of pentameric sdAb. 1V5 was analyzed by SDS-PAGE following digestion with trypsin for 0 and 2 hours (A and B respectively) and chymotrypsin for 0 and 2 h (C and D respectively).

1V5 exhibited very good resistance to digestion by trypsin and chymotrypsin. It was observed that trypsin rapidly converted 1V5 to a product with a slightly lower molecular size with no evidence of further digestion under the conditions employed (FIGS. 8A and 8B). Mass spectrometric analyses indicated that the C-terminal tags had been removed. Trypsin treatment decreased the size of the 1V5 monomer by 1602. Da which corresponds to removal of the C-terminal LISEED-LNHHHHH (SEQ ID NO.: 9) sequence (FIG. 8C) from 1V5. No cleavage products were observed following 1 h of incubation with chymotrypsin (FIGS. 8C and 8D). Mass spectrometric analyses confirmed that the bands shown in FIGS. 8C and 8D corresponded to the 1V5 monomer.

The pentameric sdAb described here displayed surprising resistance to trypsin and chymotrypsin. Although there are multiple sites for both enzymes in the pentamer, there was no any evidence of degradation by either enzyme under the conditions employed here. This observation highlights one of the advantages of single domain antibodies, the smallest antigen binding fragments from conventional antibodies, namely scFvs that contain protease-sensitive linkers. Resistance to proteases is highly desirable for in vivo applications, such as tumor imaging. In terms of conferring protease resistance, VT1B is a logical choice as an oligomerization domain because of its natural existence in digestive environments.

EXAMPLE 2

Pentabodies in which the sdAbs are Fused to the N-terminus of VT1B

To determine if the strategy described here is a generally suitable strategy for sdAb pentamerization, one can examine whether pentameric antibodies can be formed when 1) antibodies were fused to the N-terminus of VTB, 2) antibody molecules other than PTH50 are fused to VTB and 3) if mutant versions of VTB can be used as pentamerization domains.

For this purpose:

(a) Protein 1V12, which is the fusion of another sdAb molecule (PTH61), to the N-terminus of a mutant version of VTB, was constructed (FIG. 9 illustrates the primary structure. The ompA sequence is removed during secretion of the mature protein to the *E. Coli* periplasm). PTH61 is a parathyroid hormone-binding sdAb isolated from the same panning experiment as PTH50. Protein 1V12 was isolated from *E. coli* TG1 cells harboring the gene encoding for 1V12 as described for the isolation of 1V5. Size exclusion chromatography was run on a Superdex 200 column, and indicated that, as for 1V5, 1V12 forms a very homogenous pentamer (FIG. 10). Protein markers (in kDa) were run on the same column and under the same conditions. Data obtained from SPR analysis show that the protein 1V12, the pentameric form of PTH61, binds much more strongly than PTH61 to its antigen (FIG. 11, surface plasmon resonance analysis of the binding of monovalent and pentavalent (1V12) to immobilized antigen).

(b) A total of eight pentabodies (1V5, 1v11, 1V12, 1V14, PES1, PVTGL10, PJS5, PSJ6) were made using both wild type and mutant versions of VTB and with different sdAb molecules fused to either N— or to the C-terminus of VT1B. All formed pentabodies that expressed well in *E. coli* TG1 cells, have little or no sign of aggregation and which bind to their antigens with a much higher functional affinity than observed for their monomeric counterparts.

EXAMPLE 3

Construction of Decabodies

The fact that many, if not all, sdAbs can be easily pentamerized by fusing them to either the N— or to the C-terminus of different versions of VTB allows constructing decavalent antibodies by fusing one sdAb to the N-terminus and another sdAb to the C-terminus terminus of VT1B. This concept is diagrammatically illustrated in FIG. 12, a diagrammatic representation of N-terminal pentabodies, C-terminal pentabodies and a bispecific decabody. To exploit this, 1V13, a decavalent antibody, termed a decabody, was constructed. This is illustrated in FIG. 13; showing the primary structure and sequence of 1V13 and the size exclusion chromatography (Superdex 200 column, Amersham Pharmacia) of 1V12. Protein markers (in kDa) were run on the same column and under the same conditions. 1V13 has sdAb PTH22 fused to the C-terminus and sdAb PTH61 fused to the N-terminus of a D17E/W34A mutant of VT1B (FIG. 13A). PTH22 is another parathyroid hormone binding sdAb isolated from the same panning experiment as PTH50 and PTH61. 1V13 was isolated from *E. coli* TG1 cells harboring the gene encoding 1V13. Size exclusion chromatography showed that 1V13 forms a pentamer, which is however not very homogenous (FIG. 13B),

EXAMPLE 4

Improved Homogeneity of Decabodies

Because sdAbs and VT1B, the two building units for decabody construction, are very homogeneous and are expressed well in *E. coli* cells, changes are mainly made to linkers that connect the building blocks. Four new decabodies, PJR9, PJR10, PJR13 and PJR14, were constructed using different linkers, the sequences of which are shown in FIG. 14. FIG. 14 presents a comparison by size exclusion chromatography of 1V13 decavalent and its variations. The sequences of linkers connecting the sdAbs and VTB are indicated above each chromatogram. As shown in FIG. 14, the four proteins form very homogenous pentamers with no or little sign of aggregation. Protein 1V9, with the linker GPGGGGS (SEQ ID NO.: 10) to connect PTH61 and VTB and a linker AKRVAPELLGGPSG (SEQ ID NO.: 11) to connect VTB and PTH22, has the best size exclusion profile.

The concept of preparation and use of decavalent antibodies (decabodies) can be extended, according to another embodiment of the present invention, by use of known oligovalent, water soluble carbohydrate ligands analogous to the carbohydrate receptor of VT1B and which form complexes with VT1B, e.g. STARFISH—see Kitov, Pavel I. et. al., 2000, ref. 19. Since STARFISH cross-links two pentameric VT1Bs, it provides another means of making decabodies.

STARFISH will bind to the pentabodies of the present invention, but not to the individual units. Accordingly, a labeled version of STARFISH can be used for detecting the pentabodies described herein. Pentabodies bound to a target such as a type of cancer cell, a bacterial pathogen, an anthrax spore etc., will form a complex with added, labeled STARFISH to allow detection of the STARFISH-pentabody-target complex. After addition and binding of STARFISH, residual unbound STARFISH is washed out of the system, and the bound STARFISH detected by means of its label (fluorescence, radioactivity, etc.), to measure bound pentabodies. Moreover, STARFISH-type ligands can also be used in conjunction with pentabodies of the present invention in therapeutic applications. For example, one could have two separate and distinct types of self-assembly molecules according to the invention, one to recognize and to bind to the target and another to recognize and to bind to a killer cell or compound for the target. Both types form pentabodies, for strong binding. Addition of STARFISH to cause binding together of the two types of pentabodies will bring the target and killer cells into close proximity, for interaction between them.

Thus, it is apparent that there has been provided in accordance with the invention a Novel Self-Assembly Molecules that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

REFERENCES

1. Pluckthun, A and Pack, P., New protein engineering approaches to multivalent and bispecific antibody fragments . . . , *Immunotechnology* 3, (1997) 83-105.

2. Terskikh et al., "Peptabody: a new type of high avidity binding protein, *Proc. Natl. Acad. Sci.* (USA) Vol. 94, (1997) 1663-1668.

3. Efimov, V. P., Lustig, A. & Engel, J. The thrombospondin-like chains of cartilage oligomeric matrix protein are assembled by a five-stranded alpha-helical bundle between residues 20 and 83. *FEBS Left.* 341, 54-58 (1994).

4. Hudson, P. J. & Kortt, A. A. High avidity scFv multimers; diabodies and triabodies. *J. Immunol. Methods* 231, 177-189 (1999).
5. Kaminski, M. J. et. al., The role of homophilic binding in anti-tumor antibody R24 recognition of molecular surfaces, *J. Biol. Chem.*, Vol 274 No. 9 (1999) 5597-5604.
6. Soltyk, A. M. et al. A mutational analysis of the globotriaosylceramide binding sites of verotoxin VT1. *J. Biol. Chem.* 277, 5351-5359 (2002).
7. Yang, W. P. et al. CDR walking mutagenesis for the affinity maturation of a potent human anti-HIV-1 antibody into the picomolar range. *J. Mol. Biol.* 254, 392-403 (1995).
8. Schier, R. et al. Isolation of picomolar affinity anti-c-erbB-2 single-chain Fv by molecular evolution of the complementarity determining regions in the center of the antibody binding site. *J. Mol. Biol.* 263, 551-567 (1996).
9. Ohlin, M., Owman, H., Mach, M. & Borrebaeck, C. A. Light chain shuffling of a high affinity antibody results in a drift in epitope recognition. *Mol. Immunol.* 33, 47-56 (1996).
10. McCafferty, J., Griffiths, A. D., Winter, G. & Chiswell, D. J. Phage antibodies: filamentous phage displaying antibody variable domains. *Nature* 348, 552-554 (1990).
11. Griffiths, A. D. et al. Isolation of high affinity human antibodies directly from large synthetic repertoires. *EMBO J.* 13, 3245-3260 (1994).
12. Hoogenboom, H. R. & Chames, P. Natural and designer binding sites made by phage display technology. *Immunol. Today* 21, 371-378 (2000).
13. Tanha, J., Dubuc, G., Hirama, T. Narang, S. A. & MacKenzie, C. R. Selection by phage display of llama conventional $V_H$ fragments with heavy chain antibody $V_HH$ properties. *J. Immunol. Methods* 263, 97-109 (2002).
14. Ling, H. et al. Structure of the shiga-like toxin I B-pentamer complexed with an analogue of its receptor Gb3. *Biochemistry* 37, 1777-1788 (1998).
15. Sambrook, J. & Russel, D. W. Molecular Cloning, a laboratory manual.
16. Skerra, A., Pfitzinger, I. & Pluckthun, A. The functional expression of antibody Fv fragments in *Escherichia coli*: improved vectors and a generally applicable purification technique. *Biotechnology* (N.Y.) 9, 273-278 (1991).
17. Willuda et. al., High Thermal Stability is Essential for Tumor Targeting of Antibody fragments: engineering of a humanized anti-epithelial glycoprotein-2 (epithelial cell adhesion molecule) single-chain Fv Fragment, 1999 *Cancer Research* 59, 5758-5767.
18. Tanha et. al., Optimal Design Features of Camelized Human Single-Domain antibody Libraries, *J. Biol. Chem.* 276, 24774-24780.
19. Kitov, Pavel I. et. al., *Nature,* 403, February 2000, 669-672.

We claim as our invention:

1. A self assembly molecule having an affinity for one or more known targets and suitable for use in formation of a multimeric complex, comprising:

an $AB_5$-derived self-assembly unit comprising a monomer of the B subunit of an $AB_5$ toxin able to bind to another $AB_5$-derived self assembly unit comprising a monomer of the B subunit of the $AB_5$ toxin; and an interaction domain fused directly or via a linker to said monomer of the B subunit of the $AB_5$ toxin so as to enhance binding of the interaction domain to the target;

wherein said interaction domain comprises an antibody, antibody fragment, single domain antibody fragment, a single chain polypeptide of a VH or VL region of an antibody, a peptide or protein derived from a binding region of an antibody, or a molecule or binding portion thereof which specifically binds to cell surface receptors.

2. A kit comprising:

a plurality of self-assembly molecules according to claim 1; and, instructions for the use of said self-assembly molecules in the specific recognition of a marker, for the purposes of diagnosis.

3. The self-assembly molecule of claim 1 wherein the interaction domain is fused directly or through a linker at one of the N-terminus or the C-terminus of the self-assembly molecule.

4. The self-assembly molecule of claim 1 wherein the self-assembly unit is derived from verotoxin.

5. The self-assembly molecule of claim 1 wherein the self-assembly unit is derived from pertussis toxin.

6. The self-assembly molecule of claim 1 wherein the interaction domain is an single domain antibody.

7. The self-assembly molecule of claim 1 wherein the interaction domain is a cell-surface binding peptide.

8. The self-assembly molecule of claim 1 including a linker joining said interaction domain to said self-assembly unit.

9. The self assembly molecule of claim 1 further including a second interaction domain fused directly or via a linker to said self assembly unit so as to enhance binding of each interaction domain to said target, said second interaction domain comprising an antibody, antibody fragment, single domain antibody fragment, a single chain polypeptide of a VH or VL region of an antibody, a peptide or protein derived from a binding region of an antibody, or a molecule or binding portion thereof which specifically binds to cell surface receptors.

10. The self assembly molecule of claim 1 in pentameric form.

11. The self-assembly molecule of claim 9 including a linker joining said second interaction domain to said self-assembly unit.

* * * * *